United States Patent
Park et al.

(10) Patent No.: US 9,098,490 B2
(45) Date of Patent: Aug. 4, 2015

(54) GENETIC INFORMATION MANAGEMENT SYSTEM AND METHOD

(75) Inventors: Minseo Park, Seoul (KR); Woo-Yeon Kim, Seoul (KR)

(73) Assignee: SAMSUNG SDS CO., LTD., Seoul (KR)

( * ) Notice: Subject to any disclaimer, the term of this patent is extended or adjusted under 35 U.S.C. 154(b) by 859 days.

(21) Appl. No.: 13/278,791

(22) Filed: Oct. 21, 2011

(65) Prior Publication Data

US 2012/0102041 A1    Apr. 26, 2012

(30) Foreign Application Priority Data

Oct. 22, 2010  (KR) .......................... 10-2010-0103538

(51) Int. Cl.
*G06F 17/30*    (2006.01)
*G06F 19/28*    (2011.01)

(52) U.S. Cl.
CPC .......... *G06F 19/28* (2013.01); *G06F 17/30289* (2013.01); *G06F 17/30392* (2013.01)

(58) Field of Classification Search
CPC .............. G06F 17/30392; G06F 17/30; G06F 17/30002; G06F 17/303; G06F 17/30289; G06F 17/30539
USPC .......................... 707/758, 804, 755, 756, 749
See application file for complete search history.

(56) References Cited

U.S. PATENT DOCUMENTS

| | | | | |
|---|---|---|---|---|
| 5,204,663 A | * | 4/1993 | Lee .............................. | 340/5.28 |
| 6,317,750 B1 | * | 11/2001 | Tortolani et al. ..................... | 1/1 |
| 6,519,583 B1 | * | 2/2003 | Koleszar et al. ................. | 702/20 |
| 6,941,317 B1 | | 9/2005 | Chamberlin et al. | |
| 7,209,602 B2 | | 4/2007 | Kim | |
| 7,634,144 B2 | | 12/2009 | Kim | |
| 7,925,555 B2 | * | 4/2011 | Likas et al. ..................... | 705/35 |
| 8,036,496 B2 | | 10/2011 | Kim | |
| 2003/0055822 A1 | * | 3/2003 | Yu ..................................... | 707/6 |
| 2003/0055832 A1 | * | 3/2003 | Roccaforte ................... | 707/100 |
| 2003/0084023 A1 | * | 5/2003 | Koleszar et al. .................. | 707/1 |
| 2003/0223650 A1 | | 12/2003 | Kim | |

(Continued)

FOREIGN PATENT DOCUMENTS

| EP | 1571563 A2 | 9/2005 |
|---|---|---|
| KR | 1020030092955 A | 12/2003 |
| KR | 1020050082051 A | 8/2005 |

OTHER PUBLICATIONS

Communication dated Dec. 1, 2011 issued by the Korean Intellectual Property Office in counterpart Korean Patent Application No. 10-2010-0103538.

(Continued)

*Primary Examiner* — James Trujillo
*Assistant Examiner* — Fatima Mina
(74) *Attorney, Agent, or Firm* — Sughrue Mion, PLLC (57) ABSTRACT

A system and method for efficiently managing a vast amount of read data and genetic information obtained from sequencing data are provided. The system includes a parsing unit reading the read data and converting the read data into a table-embedded index, a table management unit classifying the table-embedded index into a master table which contains basic items about the genetic information and a slave table which contains additional items about the genetic information and managing the master table and the slave table, a search unit retrieving data from the master table and/or the slave table and outputting the retrieved data.

16 Claims, 5 Drawing Sheets

(56) References Cited

U.S. PATENT DOCUMENTS

| | | | |
|---|---|---|---|
| 2005/0091188 A1* | 4/2005 | Pal et al. | 707/1 |
| 2005/0182571 A1 | 8/2005 | Kim et al. | |
| 2005/0289524 A1* | 12/2005 | McGinnes | 717/140 |
| 2006/0074735 A1* | 4/2006 | Shukla et al. | 705/8 |
| 2006/0271505 A1* | 11/2006 | Vierich et al. | 707/2 |
| 2007/0061365 A1* | 3/2007 | Giegerich et al. | 707/104.1 |
| 2007/0143363 A1* | 6/2007 | Agarwal et al. | 707/203 |
| 2007/0211948 A1 | 9/2007 | Kim | |
| 2008/0077570 A1* | 3/2008 | Tang et al. | 707/5 |
| 2010/0046844 A1 | 2/2010 | Kim | |
| 2011/0055035 A1* | 3/2011 | Koskay et al. | 705/26.1 |
| 2012/0002893 A1 | 1/2012 | Kim | |

OTHER PUBLICATIONS

Kim, et al: GWB: "An integrated Software System for Managing and Analyzing Genomic Sequences", Oct. 2004, pp. 1-15.

Communication dated Jun. 28, 2012 issued by the Korean Intellectual Property Office in Korean Application No. 1020100103538.

Michele Cyran, et al, "Oracle Database Concepts", 10g Release 2 (10.2), Oct. 2005, 542 pages.

Srinivasan, et al, "Oracle8i Index-Organized Table and its Application to New Domains", Oracle Corporation, Nashua, NH, pp. 285-296.

Communication dated Nov. 14, 2013, issued by the State Intellectual Property Office of the People's Republic of China in counterpart Chinese Application No. 201110329432.3.

\* cited by examiner

TABLE DATA
INCLUDED IN INDEX

FIG. 4

MASTER TABLE

IDENTIFIER: VARCHAR2 (5)

ID: VARCHAR2 (10)
CHROMOSOME: NUMBER(2)
START POINT: NUMBER (10)
SIZE: NUMBER (2)
TYPE: VARCHAR (10)
MOD: NUMBER (2)

SLAVE TABLE

IDENTIFIER: VARCHAR2 (5)

QUALITY: VARCHAR2 (100)
SEQUENCE: VARCHAR2(100)
DISTANCE: VARCHAR (100)

FIG. 5

| 33 33 33 33 33 | → | ! ! ! ! ! |
| 33 33 33 33 34 | → | ! ! ! ! " |
| 33 33 33 33 35 | → | ! ! ! ! # |
| 33 33 33 33 36 | → | ! ! ! ! $ |

.
.
.

| 126 126 126 126 124 | → | ~ ~ ~ ~ | |
| 126 126 126 126 125 | → | ~ ~ ~ ~ } |
| 126 126 126 126 126 | → | ~ ~ ~ ~ ~ |

7,339,040,224 IDENTIFIERS

GENETIC INFORMATION MANAGEMENT SYSTEM AND METHOD

This application claims priority from Korean Patent Application No. 10-2010-0103538 filed on Oct. 22, 2010 in the Korean Intellectual Property Office, the disclosure of which is hereby incorporated by reference in its entirety.

BACKGROUND OF THE INVENTION

1. Field of the Invention

The present invention relates to bioinformatics technology, and more particularly, to a system and method for efficiently managing a vast amount of read data and genetic information obtained from the read data.

2. Description of the Related Art

Recently, research and development in the genome technology of the bio-industry has been increasing. Major global companies such as "Genome Quest," "Knome," and "Complete Genomics" have commercialized DNA sequencing technology called "next-generation sequencing (NGS)" and are providing NGS services. In Korea, a company called "Tera-gen" has recently launched a similar service. The NGS technologies have many potential uses in various fields including a genome field for displaying data extracted through NGS, a bio-industry field for providing genome analysis services, a genome research field for providing data, and a medical field that utilizes genome data in diagnosis and treatment.

The amount of data obtained using next-generation DNA sequencing technology is vast. For example, approximately 3.5 billion pieces of data are obtained from one human sample. For efficient analysis, retrieval, and display of the obtained data, it is very important to develop database establishment and data processing technology (that is, genetic information management technology).

Conventional genetic information management technologies include sequence alignment/map (SAM) tools, generic genome browser (GBrowse), and integrative genomics viewer (IGV).

SAM tools were published in an academic journal "Bioinformatics" in 2009 and suggest a method of effectively storing read data obtained through NGS. In SAM tools, SAM and binary alignment/map (BAM) file formats are suggested. These file formats offer a way to reduce total data size and extract data within a short period of time.

In the SAM file format, a header section is indicated by character '@,' and real data is tab-delimited and includes a total of eleven essential columns as shown in Table 1.

TABLE 1

| # | Name | Description |
|---|---|---|
| 1 | QNAME | Query NAME of the read of the read pair |
| 2 | FLAG | bitwise FLAG (pairing, strand, mate strand, etc.) |
| 3 | RNAME | Reference sequence NAME |
| 4 | POS | 1-based leftmost POSition of clipped alignment |
| 5 | MAPQ | MAPping Quality (Phred-scaled) |
| 6 | CIGAR | extended CIGAR string (operations: MIDNSHP) |
| 7 | MRNM | Mate Reference NaMe ('=' if same as RNAME) |
| 8 | MPOS | 1-based leftmost Mate POSition |
| 9 | ISIZE | inferred Insert SIZE |
| 10 | SEQ | query SEQuence on the same strand as the reference |
| 11 | QUAL | query QUALity (ASCII-33 = Phred based quality) |

The SAM format can be converted into the BAM format which is a binary format. This enables rapid extraction of information from data and reduction of data space. To actually access data, a specially designed program called "samtools" should be used.

GBrowse is a genetic information browser utilized by many research institutes worldwide. Although GBrowse is based on a database called MySQL, it can also manage file-based data. However, it cannot store/manage read data in the database. In addition, since the volume of NGS data is far larger than that of general genetic information, GBrowse cannot be applied as it is to the NGS data. Therefore, attempts were made in 2009 to display the NGS data, and as a result, GBrowse has been modified to be able to display the read data.

Lastly, IGV is a browser developed to display genetic information on a local computer. IGV is designed to include not only the NGS data but also experimental data such as a microarray. In the case of the NGS data, data in the SAM or BAM file format may be received as inputs. A user may install this tool in his or her computer, obtain a necessary file, and import the file to the tool.

The above conventional technologies have the following problems.

First, it is almost impossible to modify only a desired part of data used in the conventional technologies. To modify a part of the data, the entire data must be generated again. Thus, data should be generated in the SAM format and then converted into the BAM file which is a binary format. Therefore, any modification of data requires the entire file to be generated again.

Second, it is difficult with the conventional technologies to determine redundancy of data in the entire data when generating or additionally deleting the data. When a piece of data is modified, the entire data must be checked to find redundancy of the piece of data in the entire data. In addition, when necessary data is extracted from the entire data, the entire data must be checked to find redundancy of the extracted data.

Third, the conventional technologies are not intended for multiple users. Therefore, when multiple users simultaneously access the same data, the data accesses cannot be controlled, nor can necessary rules be applied. Hence, a specific program should be devised to handle the simultaneous same data accesses by the multiple users.

Fourth, data integrity processing is difficult with the conventional technologies. Data integrity is about preventing an unauthorized user from modifying or deleting data in an unauthorized way. For data integrity, each piece of data must be associated with a system account, or a special tool for managing the data must be developed. The security of genetic information of living things is very important. In particular, human genetic information must be protected with a higher level of security than that of resident registration numbers of individuals. Therefore, the difficulty of integrity processing can be pointed to as a clear problem.

Lastly, the conventional technologies do not have the function of recovering data when the data is damaged due to various reasons. Therefore, a data recovery related function must be implemented, or a data recovery related program must be operated. In industrial aspects, data stability is a crucial issue in addition to data integrity.

SUMMARY OF THE INVENTION

The present invention has been made to solve the foregoing problems of the prior art and therefore an aspect of the present invention is to design a database which can process large-volume genetic information, such as next-generation sequencing (NGS) read data, in a rapid and stable manner. In particular, an aspect of the present invention is to effectively apply the database when a genome browser displays data.

However, aspects of the present invention are not restricted to the one set forth herein. The above and other aspects of the present invention will become more apparent to one of ordinary skill in the art to which the present invention pertains by referencing the detailed description of the present invention given below.

According to an aspect of the present invention, there is provided a genetic information management system for building a database of genetic information by processing read data obtained from a genome analyzer and outputting database search results in response to a user's command, and the system comprises a parsing unit reading the read data and converting the read data into a table-embedded index; a table management unit classifying the table-embedded index into a master table which contains basic items of the record and a slave table which contains additional items of the record, and managing the master table and the slave table; and a search unit retrieving data from the master table and/or the slave table and outputting the retrieved data.

According to another aspect of the present invention, there is provided a genetic information management system building a database of genetic information by processing read data obtained from a genome analyzer and outputting database search results in response to a user's command, and the system comprises a parsing unit reading the read data and converting the read data into a table-embedded index; and a search unit searching the table-embedded index using a primary key related to the user's command, wherein the primary key includes at least a part of ASCII codes.

According to another aspect of the present invention, there is provided a genetic information management system building a database of genetic information by processing read data obtained from a genome analyzer and outputting database search results in response to a user's command, and the system comprises a parsing unit reading the read data and converting the read data into a data format in the form of a table-embedded index; a table management unit storing and managing the data format; and a search unit retrieving data from the data format on the basis of a primary key and outputting the retrieved data.

According to another aspect of the present invention, there is provided a genetic information management method of building a database of genetic information by processing read data obtained from a genome analyzer and outputting database search results in response to a user's command, and the method comprises reading the read data; generating from the read data a master table which contains basic items about the genetic information; generating from the read data a slave table which contains additional items about the genetic information; and retrieving data from the master table and/or the slave table and outputting the retrieved data, wherein the master table and the slave table constitute a table-embedded index.

BRIEF DESCRIPTION OF THE DRAWINGS

The above and other aspects and features of the present invention will become more apparent by describing in detail exemplary embodiments thereof with reference to the attached drawings, in which.

DETAILED DESCRIPTION OF THE INVENTION

The present invention will now be described more fully hereinafter with reference to the accompanying drawings, in which preferred embodiments of the invention are shown. This invention may, however, be embodied in different forms and should not be construed as limited to the embodiments set forth herein. Rather, these embodiments are provided so that this disclosure will be thorough and complete, and will convey the scope of the invention to those skilled in the art. The same reference numbers indicate the same components throughout the specification.

In the development of a browser that displays genetic information, a method of effectively storing read data extracted using next-generation sequencing (NGS) technology is required. DNA sequencing performed on one human sample (human genome) using the NGS technology may produce more than approximately 800 GB of read data. To display such a vast amount of data on a browser in real time, it is crucial to process the data efficiently. In this regard, the present invention suggests a method of storing/retrieving read data and genetic information, which is obtained from the read data, in/from a database.

Figure 1:
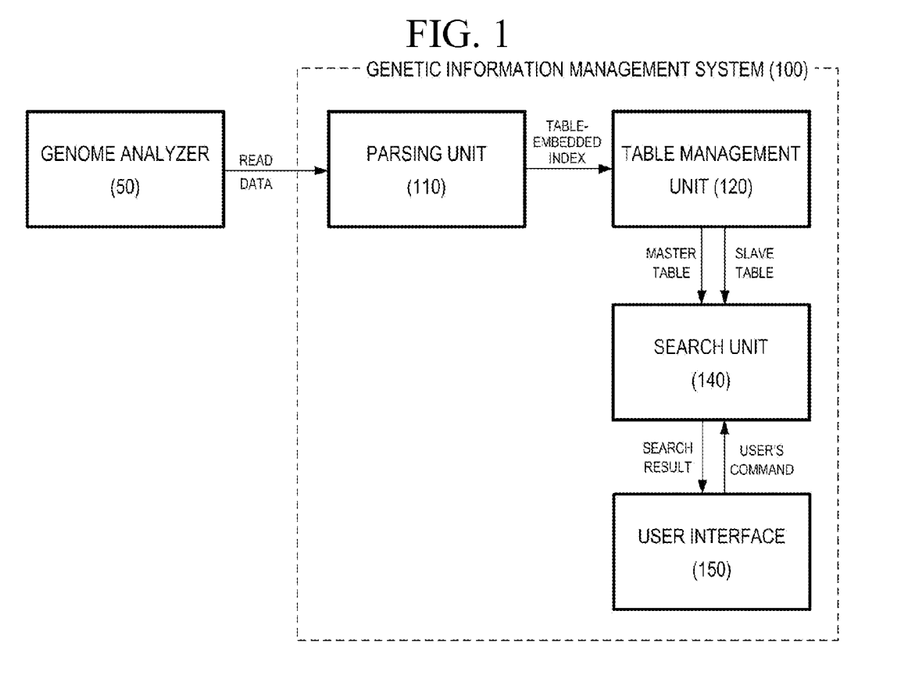
FIG. 1 is a block diagram of a genetic information management system according to an embodiment of the present invention.

FIG. 1 is a block diagram of a genetic information management system 100 according to an embodiment of the present invention. Referring to FIG. 1, the genetic information management system 100 may include a parsing unit 110, a table management unit 120, a search unit 140, and a user interface 150. In the embodiment of FIG. 1, a genome analyzer 50 is installed outside the genetic information management system 100. However, the genome analyzer 50 can also be installed inside the genetic information management system 100 without departing from the spirit of the present invention.

The genetic information management system 100 builds a database of genetic information by processing read data obtained from the genome analyzer 50 and outputs database search results in response to a user's command.

Figure 2:
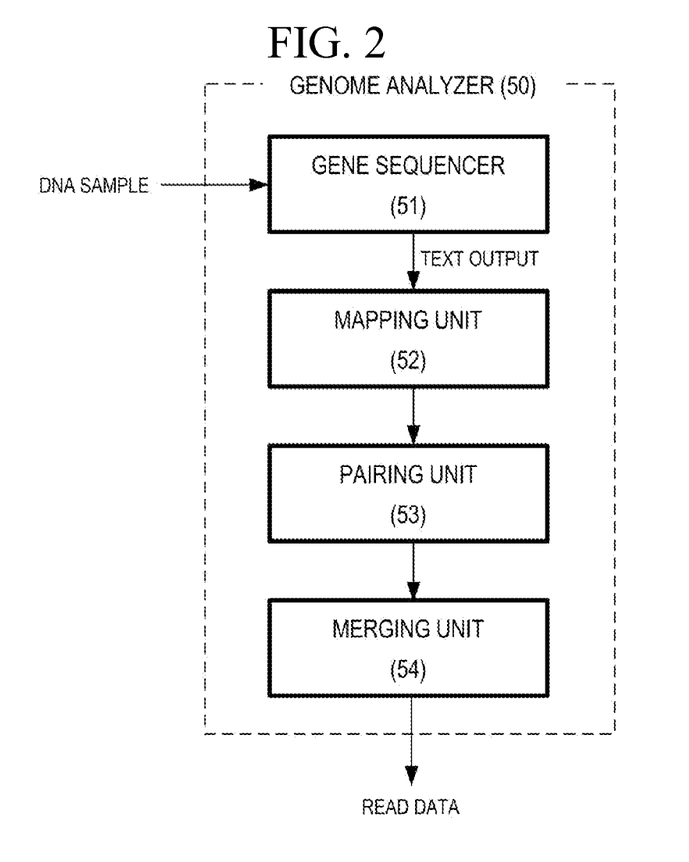
FIG. 2 is a block diagram of a genome analyzer according to an embodiment of the present invention.

Referring to FIG. 2, the genome analyzer 50 generates read data, which is to be provided to the genetic information management system 100, from a DNA sample. The genome analyzer 50 may include a gene sequencer 51, a mapping unit 52, a pairing unit 53, and a merging unit 54.

The gene sequencer 51 generates a text output from a DNA sample. The text output may include read (sequencing data) and read quality data. To generate the text output, the gene sequencer 51 may, for example, attach a gene, which is to be analyzed, to a bead existing in a flow cell, treat the flow cell with a chemical substance (e.g., a fluorescent substance) to change the color of the bead according to bases A, T, G and C, and photograph the color of the bead using an optical microscope.

The mapping unit 52 maps the text output to a reference genome. The reference genome is a genome sequence that has already been revealed. For the human genome, information available in the National Center for Biology Information (NCBI) can be referenced.

The pairing unit 53 connects read data that forms a pair. Lastly, the merging unit 54 merges obtained pairing data into one file for each sample. Each sample undergoes a number of tests for the sake of accuracy, and the merging unit 54 merges data resulting from these tests. The merging process is optional. Through the above processes, output data (that is, read data to be provided to the genetic information management system 100) of the genome analyzer 50 is obtained.

Referring back to FIG. 1, the parsing unit 110 reads the read data provided by the genome analyzer 50 and converts the read data into a database-based, table-embedded index. The table-embedded index may be expressed as an index-organized table (IOT) in Oracle database, as a clustered index in MS-SQL and SYBASE, and as an InnoDB in MySQL.

As described above, the present invention uses a database-based system instead of a conventional file-based system. The database-based system has various advantages over the conventional file-based system, such as modification of a data structure, avoidance of data redundancy, ease of concurrency control, ease of integrity processing, and ease of recovery processing. A genome browser is a browser that displays a large amount of genome information. Thus, data redundancy must be avoided, and concurrency control and modification of a data structure frequently occur in the genome browser. In addition, since the security of genetic information, which is unique information, is important, the database-based system that can perform integrity processing with ease is more suitable for the genetic information. Also, there exists a possibility that the genome browser will additionally generate a large amount of data in response to a user's command, leading to modification of a data structure. From this perspective, the database-based system that can modify a data structure is more effective.

In addition to using the database-based system, the present invention uses a table-embedded index (instead of a conventional table) in building a database.

Read data presented in a table typically has a small number of columns and a very large number of rows (3.5 billion rows in the case of a human sample). Table 2 below is a typical table of read data used in a conventional genome browser. Here, the numbers in brackets refer to the number of bytes.

TABLE 2

| Primary key (5) | ID (10) | Chromosome number (2) | Start point (10) | Size (2) | Type (10) | Mod (2) | Quality file (100) | Sequence (100) | Distance (100) |
|---|---|---|---|---|---|---|---|---|---|
| ... | | | | | | | | | |
| ... | | | | | | | | | |
| 3.5 billion rows | | | | | | | | | |

Considering these properties of the read data, the present invention suggests a table-embedded index. The table-embedded index overcomes a disadvantage of a conventional table, that is, complements a process of reading the table twice when accessing records using an index.

Figure 3A:
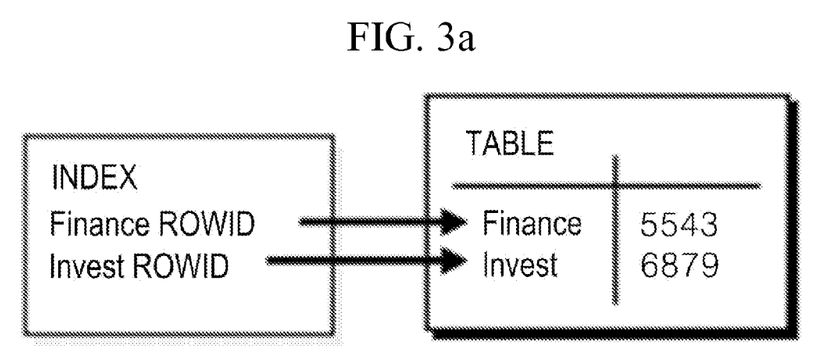
FIG. 3A is a diagram illustrating a conventional table structure in which an index is separated from a table.
Figure 3B:
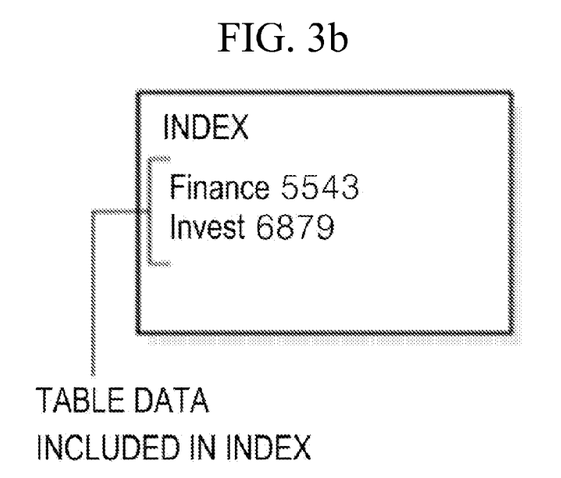
FIG. 3B is a diagram illustrating an example of a table-embedded index in contrast with FIG. 3A.

FIG. 3A is a diagram illustrating an example of a conventional table structure in which an index is separated from a table. FIG. 3B is a diagram illustrating an example of a table-embedded index in contrast with FIG. 3A. In the case of the conventional table of FIG. 3A, ROWID is obtained by searching an index using a primary key, and then the table is read using the ROWID. Therefore, primary keys of a key column are redundantly stored both in the index and the table, thereby wasting disk space and increasing search time.

On the other hand, in the case of the table-embedded index of FIG. 3B, there is no need to store primary keys redundantly. In particular, the table-embedded index is more effective as the number of rows recorded increases. For example, read data of a human genome includes more than 6 billion pieces of data (based on 30×). Therefore, the number of rows is very large, and accordingly the number of primary keys to be recorded is large. Thus, in the case of genome data, the conventional table structure that requires two search processes performed using a primary key and has redundant storage spaces severely degrades the performance of a genome browser. This increases the need for a structure in which a data table is included in an index, that is, a table-embedded index. Examples of the table-embedded index include an IOT of Oracle database, a clustered index of MS-SQL and SYBASE, and an InnoDB of MySQL.

Referring back to FIG. 1, the table management unit 120 divides the table-embedded index obtained from the parsing unit 110 into a master table which contains basic items about genetic information and a slave table which contains additional items about the genetic information and manages the table-embedded index accordingly. Although the table-embedded index can reduce storage space and is an efficient index that can improve the performance of the genome browser, it still has disadvantages. If one column of the table-embedded index is too large or if the number of columns in the table-embedded index is too large, efficiency may significantly degrade. Thus, for example, quality data containing a large number of bytes needs to be separated from other data in the genetic information. The quality data is information that can be omitted from a main browser page, that is, data that can be shown only in a detailed browser page.

Figure 4:
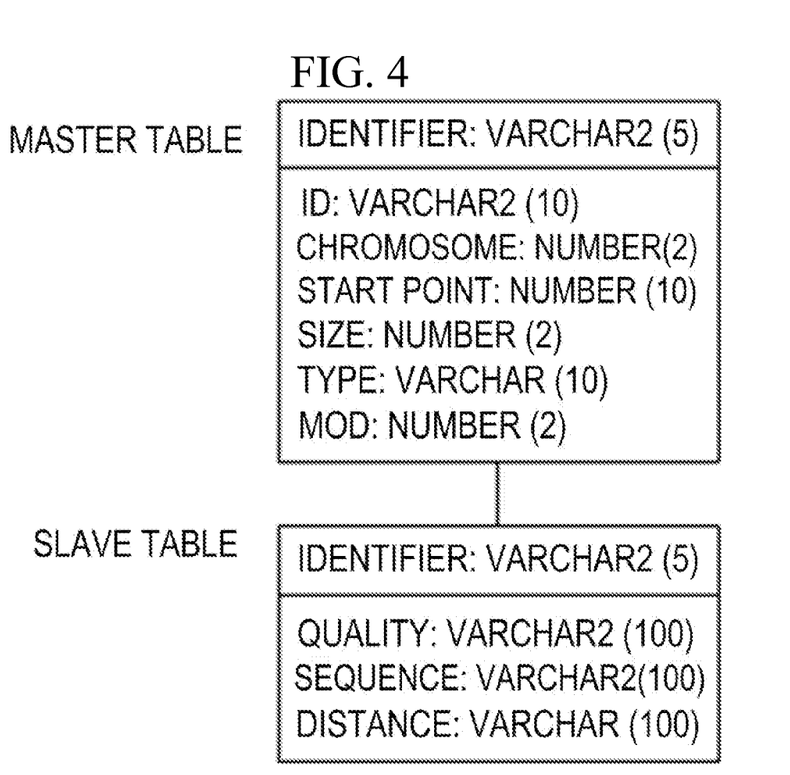
FIG. 4 is a diagram illustrating examples of basic items stored in a master table and additional items stored in a slave table.

Examples of the basic items stored in the master table and those of the additional items stored in the slave table are illustrated in FIG. 4. The additional items are data items that have relatively large data sizes and that can be omitted from the main browser. The master table and the slave table include the same primary keys and are searched and combined using the same primary keys.

Referring back to FIG. 1, the user interface 150 receives a user's command, transmits the user's command to the search unit 140, and displays search results of the search unit 140 for the user. The user interface 150 may be implemented as, but not limited to, a genome browser.

The search unit 140 retrieves data from the master table and/or the slave table and outputs the retrieved data in response to a user's command. When the user's command is a ZoomOut command, the search unit 140 retrieves data corresponding to a primary key related to the user's command from the master table and outputs the retrieved data. When the user's command is a ZoomIn command, the search unit 140 retrieves data corresponding to the primary key from the master table and data corresponding to the primary key from the slave table and outputs a combination of the retrieved data.

The genome browser (included in the user interface 150) has a different amount of data to be arranged for each section of a data search range. Therefore, setting a different table for each section may be effective. The genome browser typically has a Zoom In function and a Zoom Out function. The Zoom In function of the genome browser limits a portion of genetic information which is displayed to about 100 kilobases (KB) in order to show the genetic information in detail. Although the Zoom In function limits the genetic information of the read data to be displayed, it may lead to the display of more detailed information about a piece of read data, that is, using a combination of data of the master table and data of the slave table.

On the other hand, a portion of the genetic information displayed by the Zoom Out function is about 10 megabases (MB). Thus, a relatively large amount of genetic information of the read data is displayed. In this case, only the master table may be referred to in order to display the basic items. If the genetic information does not have the master table/slave table structure, even when a user frequently uses the Zoom In function and the Zoom Out function, one integrated table may be referred to. However, since one integrated table includes many items of large bytes as described above, the efficiency of the table-embedded index may decrease.

Meanwhile, inefficiency created in the process of combining data of the master table and data of the slave table must be taken into consideration. However, establishing the master table and the slave table in the form of the table-embedded index reduces search time and does not require a large number of rows to be considered since a small range (e.g., 100 KB) is processed. Thus, inefficiency due to the combining process is not great.

As described above, in a double-table structure which includes the master table and the slave table, a common key (primary key) is needed to search and combine the two tables. However, since each sample produces approximately 3.5 billion pieces of read data, an addition of only 1 byte to the primary key may result in an addition of approximately 3.5 gigabytes. For this reason, a method of putting more than 3.5 billion pieces of data in a short key is required.

Accordingly, the present invention suggests a method of forming the common primary key using at least some of American Standard Code for Information Interchange (ASCII) codes. For example, ASCII characters corresponding to ASCII codes 33 to 126 may be combined to represent a primary key. Table 3 below shows ASCII codes and decimal numbers corresponding to the ASCII codes.

TABLE 3

| ASCII | Decimal |
| --- | --- |
| NULL | 0 |
| SOH | 1 |
| STX | 2 |
| ETX | 3 |
| EOT | 4 |
| ENQ | 5 |
| ACK | 6 |
| BEL | 7 |
| BS | 8 |
| HT | 9 |
| LF | 10 |
| VT | 11 |
| FF | 12 |
| CR | 13 |
| SO | 14 |
| SI | 15 |
| DLE | 16 |
| DC1 | 17 |
| SC2 | 18 |
| SC3 | 19 |
| SC4 | 20 |
| NAK | 21 |
| SYN | 22 |
| ETB | 23 |
| CAN | 24 |
| EM | 25 |
| SUB | 26 |
| ESC | 27 |
| FS | 28 |
| GS | 29 |
| RS | 30 |
| US | 31 |
| SP | 32 |
| ! | 33 |
| " | 34 |
| # | 35 |
| $ | 36 |
| % | 37 |
| & | 38 |
| ' | 39 |
| ( | 40 |
| ) | 41 |
| * | 42 |
| + | 43 |
| , | 44 |
| - | 45 |
| . | 46 |
| / | 47 |
| 0 | 48 |
| 1 | 49 |
| 2 | 50 |
| 3 | 51 |
| 4 | 52 |
| 5 | 53 |
| 6 | 54 |
| 7 | 55 |
| 8 | 56 |
| 9 | 57 |
| : | 58 |
| ; | 59 |
| < | 60 |
| = | 61 |
| > | 62 |
| ? | 63 |
| @ | 64 |
| A | 65 |
| B | 66 |
| C | 67 |
| D | 68 |
| E | 69 |
| F | 70 |
| G | 71 |
| H | 72 |
| I | 73 |
| J | 74 |
| K | 75 |
| L | 76 |
| M | 77 |
| N | 78 |
| O | 79 |
| P | 80 |
| Q | 81 |
| R | 82 |
| S | 83 |
| T | 84 |
| U | 85 |
| V | 86 |
| W | 87 |
| X | 88 |
| Y | 89 |
| Z | 90 |
| [ | 91 |
| \ | 92 |

TABLE 3-continued

| ASCII | Decimal |
|---|---|
| ] | 93 |
| ^ | 94 |
| _ | 95 |
| ` | 96 |
| a | 97 |
| b | 98 |
| c | 99 |
| d | 100 |
| e | 101 |
| f | 102 |
| g | 103 |
| h | 104 |
| i | 105 |
| j | 106 |
| k | 107 |
| l | 108 |
| m | 109 |
| n | 110 |
| o | 111 |
| p | 112 |
| q | 113 |
| r | 114 |
| s | 115 |
| t | 116 |
| u | 117 |
| v | 118 |
| w | 119 |
| x | 120 |
| y | 121 |
| z | 122 |
| { | 123 |
| | | 124 |
| } | 125 |
| ~ | 126 |
| DEL | 127 |

ASCII codes 33 to 126 are general characters, and the other 34 ASCII codes are control characters. Therefore, ASCII characters corresponding to the ASCII codes 33 to 126 may be combined to represent a primary key.

Figure 5:
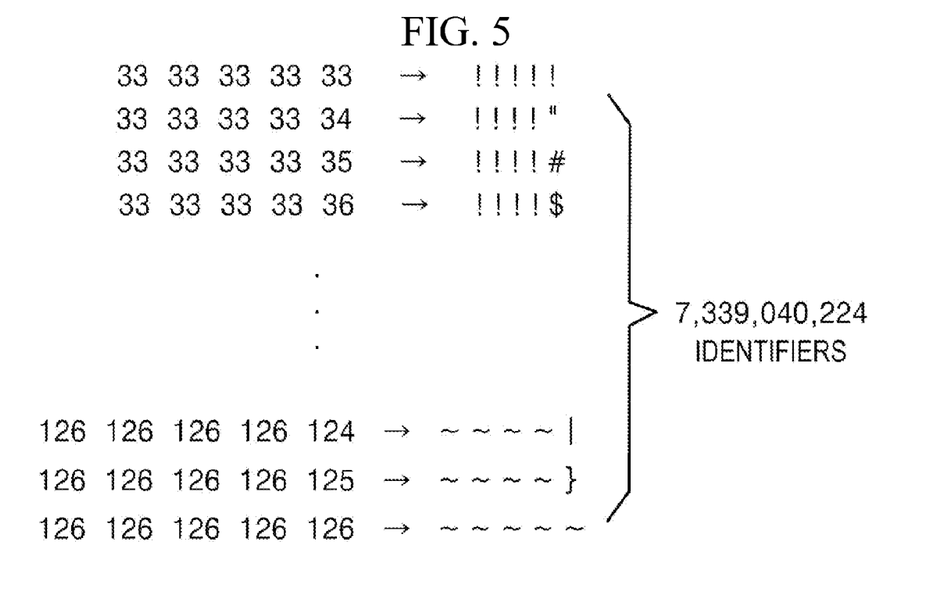
FIG. 5 is a diagram illustrating 7.3 billion identifiers generated using American Standard Code for Information Interchange (ASCII) characters of 5 bytes.

Referring to FIG. 5, if a primary key is represented in 5 bytes using the ASCII codes in the range from 33 to 126, 7.3 billion identifiers can be generated using only 5 bytes. Generating as many identifiers as possible using a small number of bytes is not just required in the double-table structure that includes the master table and the slave table. It may also be used to reduce the size of a master key contained in a table in an embodiment in which a single table (in the form of a table-embedded index only) obtained from the parsing unit 110 of FIG. 1 is searched by the search unit 140.

According to the present invention, large-volume genetic information such as NGS read data can be processed with improved performance. In particular, the application of a table-embedded index to large-volume genetic information increases storage space and data processing speed, and separation of tables reduces the search time. Furthermore, since ASCII code-based identifiers are used, the time required to search data and combine tables can be reduced.

Therefore, the present invention can be widely used to process large-volume data for purposes of providing genome analysis services (sequencing a genome and displaying the sequencing results on a gene browser), for research purposes (extracting DNA from various samples and analyzing the extracted data) for medical purposes (diagnosis and treatment), and also for other purposes.

Each component described above with reference to FIGS. 1 and 2 may be implemented as a software component, such as a task, a class, a subroutine, a process, an object, an execution thread or a program performed in a predetermined region of a memory, or a hardware component, such as a Field Programmable Gate Array (FPGA) or Application Specific Integrated Circuit (ASIC). In addition, the components may be composed of a combination of the software and hardware components. The components may be reside on a computer-readable storage medium or may be distributed over a plurality of computers. Functions provided in the respective components may be separated into further detailed components or combined into one component performing a plurality of functions.

In concluding the detailed description, those skilled in the art will appreciate that many variations and modifications can be made to the preferred embodiments without substantially departing from the principles of the present invention. Therefore, the disclosed preferred embodiments of the invention are used in a generic and descriptive sense only and not for purposes of limitation.

What is claimed is:

1. A genetic information management system for building a database of genetic information by processing read data obtained from a genome analyzer and outputting database search results in response to a user's command, the system comprising:
   a processor;
   a parsing unit executed by the processor and reading the read data and converting the read data into a table-embedded index having a structure in which a data table is included in an index;
   a table management unit executed by the processor and dividing the table-embedded index into a master table which contains basic items about the genetic information and a slave table which contains additional items about the genetic information, and managing the master table and the slave table; and
   a search unit executed by the processor and retrieving data from the master table and/or the slave table and outputting the retrieved data,
   wherein each of the master table and the slave table comprises primary keys, and the search unit searches the master table and the slave table using a primary key related to the user's command, and
   wherein the search unit retrieves data corresponding to the primary key from the master table and outputs the retrieved data when the user's command is a ZoomOut command, and retrieves data corresponding to the primary key from the master table and data corresponding to the primary key from the slave table and outputs a combination of the retrieved data corresponding to the primary key from the master table and the retrieved data corresponding to the primary key from the slave table when the user's command is a ZoomIn command.

2. The system of claim 1, wherein the table-embedded index is an index-organized table (TOT), a clustered index, or an InnoDB.

3. The system of claim 1, wherein the basic items comprise the ID, chromosome number, start point, type and mod of the genetic information, and the additional items comprise the quality, sequence, and differences of the genetic information.

4. The system of claim 1, wherein the primary key includes at least a part of American Standard Code for Information Interchange (ASCII) codes.

5. The system of claim 4, wherein the at least a part of the ASCII codes comprises ASCII codes in a range from 33 to 126.

6. The system of claim 5, wherein the primary key is represented in 5 bytes generated by combining the ASCII codes in the range from 33 to 126.

7. A genetic information management system building a database of genetic information by processing read data obtained from a genome analyzer and outputting database search results in response to a user's command, the system comprising:
   a processor;
   a parsing unit executed by the processor and reading the read data and converting the read data into a table-embedded index having a structure in which a data table is included in an index;
   a table management unit executed by the processor and dividing the table-embedded index into a master table containing basic items about the genetic information and a slave table containing additional items about the genetic information; and
   a search unit executed by the processor and searching the table-embedded index using a primary key related to the user's command,
   wherein the primary key includes at least a part of ASCII codes,
   wherein each of the master table and the slave table comprises primary keys, and the search unit searches the master table and the slave table using a primary key related to the user's command, and
   wherein the search unit retrieves data corresponding to the primary key from the master table and outputs the retrieved data when the user's command is a ZoomOut command, and retrieves data corresponding to the primary key from the master table and data corresponding to the primary key from the slave table and outputs a combination of the retrieved data corresponding to the primary key from the master table and the retrieved data corresponding to the primary key from the slave table when the user's command is a ZoomIn command.

8. The system of claim 7, wherein the at least a part of the ASCII codes comprises ASCII codes in a range from 33 to 126.

9. The system of claim 8, wherein the primary key is represented in 5 bytes generated by combining the ASCII codes in the range from 33 to 126.

10. A genetic information management system building a database of genetic information by processing read data obtained from a genome analyzer and outputting database search results in response to a user's command, the system comprising:
   a processor;
   a parsing unit executed by the processor and reading the read data and converting the read data into a data format in the form of a table-embedded index having a structure in which a data table is included in an index;
   a table management unit executed by the processor and storing and managing the data format and dividing the data format in the table-embedded index into a master table containing basic items about the genetic information and a slave table containing additional items about the genetic information; and
   a search unit executed by the processor and retrieving data from the data format on the basis of a primary key and outputting the retrieved data in response to the user's command,
   wherein the search unit retrieves data corresponding to the primary key from the max master table and outputs the retrieved data when the user's command is a ZoomOut command, and the search unit retrieves data corresponding to the primary key from the master table and data corresponding to the primary key from the slave table and outputs a combination of the retrieved data corresponding to the primary key from the master table and the retrieved data corresponding to the primary key from the slave table when the user's command is a ZoomIn command.

11. A genetic information management method of building a database of genetic information by processing read data obtained from a genome analyzer and outputting database search results in response to a user's command, the method comprising:
   reading the read data;
   converting the read data into a table-embedded index having a structure in which a data table is included in an index;
   generating from the table-embedded index a master table which contains basic items about the genetic information;
   generating from the table-embedded index a slave table which contains additional items about the genetic information; and
   retrieving data from the master table and/or the slave table and outputting the retrieved data,
   wherein the master table and the slave table constitute a table-embedded index,
   wherein each of the master table and the slave table comprises primary keys, and
   wherein the method further comprises:
      searching the master table and the slave table using a primary key related to the user's command;
      retrieving data corresponding to the primary key from the master table and outputting the retrieved data when the user's command is a ZoomOut command; and
      retrieving data corresponding to the primary key from the master table and data corresponding to the primary key from the slave table and outputting a combination of the retrieved data corresponding to the primary key from the master table and the retrieved data corresponding to the primary key from the slave table when the user's command is a ZoomIn command.

12. The method of claim 11, wherein the table-embedded index is an IOT, a clustered index, or an InnoDB.

13. The method of claim 11, wherein the basic items comprise the ID, chromosome number, start point, type and mod of the genetic information, and the additional items comprise the quality, sequence, and differences of the genetic information.

14. The method of claim 11, wherein the primary key includes at least a part of ASCII codes.

15. The method of claim 14, wherein the at least a part of the ASCII codes comprises ASCII codes in a range from 33 to 126.

16. The method of claim 15, wherein the primary key is represented in 5 bytes generated by combining the ASCII codes in the range from 33 to 126.

* * * * *